(12) United States Patent
Hille

(10) Patent No.: US 11,173,088 B2
(45) Date of Patent: Nov. 16, 2021

(54) RECLINING FURNITURE COMPRISING A WARNING DEVICE, AND METHOD FOR OPERATING A WARNING DEVICE OF A RECLINING FURNITURE

(71) Applicant: DewertOkin GmbH, Kirchlengern (DE)

(72) Inventor: Armin Hille, Bielefeld (DE)

(73) Assignee: DewertOkin Technology Group Co., Ltd, Jiaxing (CN)

( * ) Notice: Subject to any disclaimer, the term of this patent is extended or adjusted under 35 U.S.C. 154(b) by 138 days.

(21) Appl. No.: 16/481,379

(22) PCT Filed: Jan. 25, 2018

(86) PCT No.: PCT/EP2018/051824
§ 371 (c)(1),
(2) Date: Jul. 26, 2019

(87) PCT Pub. No.: WO2018/138196
PCT Pub. Date: Aug. 2, 2018

(65) Prior Publication Data
US 2020/0000666 A1 Jan. 2, 2020

(30) Foreign Application Priority Data

Jan. 27, 2017 (DE) ...................... 10 2017 101 647.3

(51) Int. Cl.
*A61G 12/00* (2006.01)
*A47C 1/02* (2006.01)
(Continued)

(52) U.S. Cl.
CPC ................ *A61G 12/00* (2013.01); *A47C 1/02* (2013.01); *A47C 1/0242* (2013.01); *A47C 7/62* (2013.01); *G08B 21/02* (2013.01)

(58) Field of Classification Search
CPC .... A61G 12/00; A47C 1/0242; A47C 20/041; A47C 1/03211; A47C 7/62; A47C 1/02;
(Continued)

(56) References Cited

U.S. PATENT DOCUMENTS

| 5,780,798 A | 7/1998 | Hall-Jackson |
| 6,078,261 A * | 6/2000 | Davsko ................. A61B 5/1115 |
| | | 200/85 R |

(Continued)

FOREIGN PATENT DOCUMENTS

| DE | 102009010379 | 10/2009 |
| DE | 202008018080 | 8/2011 |

(Continued)

*Primary Examiner* — Milton Nelson, Jr.
(74) *Attorney, Agent, or Firm* — Henry M. Feiereisen LLC

(57) ABSTRACT

The invention relates to reclining furniture comprising at least one sensor (6) and a warning device coupled to said sensor in order to warn about an undesired standing process of a user of the reclining furniture. The reclining furniture is characterized in that the warning device is designed to evaluate information of the at least one sensor (6) with respect to a movement and/or behavior pattern of a person using the reclining furniture in order to emit a warning signal as soon as there is an intention to leave the reclining furniture. The invention additionally relates to a method for operating a warning device of reclining furniture, said warning device being coupled to at least one sensor (6) which is arranged on the reclining furniture.

15 Claims, 1 Drawing Sheet

(51) Int. Cl.
*A47C 7/62* (2006.01)
*G08B 21/02* (2006.01)
*A47C 1/024* (2006.01)

(58) Field of Classification Search
CPC ......... A47C 7/72; G08B 21/02; A61B 5/1115;
A61B 5/6891
See application file for complete search history.

(56) References Cited

U.S. PATENT DOCUMENTS

| | | | |
|---|---|---|---|
| 9,351,890 B2* | 5/2016 | Hough | A61G 5/127 |
| 2003/0095263 A1 | 5/2003 | Varshneya et al. | |
| 2016/0022039 A1* | 1/2016 | Paul | A47C 1/0342 |
| | | | 297/88 |
| 2016/0128610 A1 | 5/2016 | Kostic et al. | |
| 2016/0140827 A1* | 5/2016 | Derenne | A61B 5/747 |
| | | | 340/573.7 |
| 2016/0310067 A1* | 10/2016 | Heinrich | A61B 5/02055 |
| 2016/0354263 A1 | 12/2016 | Furman et al. | |
| 2017/0365148 A1* | 12/2017 | Rosenfeld | G08B 21/0446 |
| 2018/0068545 A1* | 3/2018 | Kusens | G06T 7/20 |
| 2018/0078180 A1* | 3/2018 | Allen | A61B 5/1115 |

FOREIGN PATENT DOCUMENTS

| | | |
|---|---|---|
| WO | WO 2016/123339 | 8/2016 |
| WO | WO 2016/156779 | 10/2016 |

\* cited by examiner

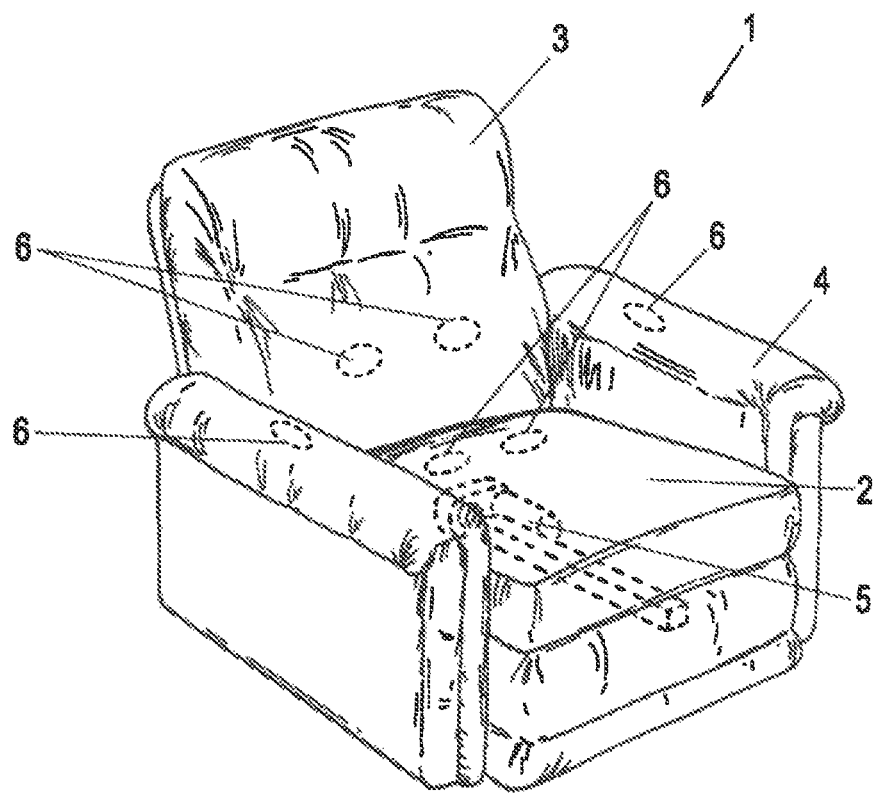

RECLINING FURNITURE COMPRISING A WARNING DEVICE, AND METHOD FOR OPERATING A WARNING DEVICE OF A RECLINING FURNITURE

CROSS-REFERENCES TO RELATED APPLICATIONS

This application is the U.S. National Stage of International Application No. PCT/EP2018/051824, filed Jan. 25, 2018, which designated the United States and has been published as International Publication No. WO 2018/138196 A1 and which claims the priority of German Patent Application, Serial No. 10 2017 101 647.3, filed Jan. 27, 2017, pursuant to 35 U.S.C. 119(a)-(d).

BACKGROUND OF THE INVENTION

The invention relates to reclining furniture having at least one sensor and a warning device coupled to said sensor in order to warn about an undesired rising of a user of the reclining furniture. The invention also relates to a method for operating such a warning device of a reclining furniture.

Particularly in the nursing or hospital sector, it may be desirable for the nursing staff to be informed when a user of the reclining furniture gets up, for example in order to prevent a possible fall after getting up. In this context, seating furniture such as recliners, but also loungers or beds are to be regarded as reclining furniture.

From the publication U.S. Pat. No. 5,780,798 A, a bed is known as reclining furniture of this kind, in which sensors are arranged under a mattress, which switch depending on a weight resting on the mattress. The sensors are connected to a warning device which emits an audible and/or visible alarm signal if the sensors do not indicate the presence of a person in the bed, Le, if the user has left the bed.

In a similar way, a known piece of reclining furniture with an electromotive furniture drive is known from the publication DE 20 2008 018 080 U1 in which a strain measuring device is inserted into the electromotive furniture drive in order to determine whether a person uses the piece of furniture or not. In turn, a warning device can be used to issue a warning when a user or patient leaves the bed so that nursing staff can prevent a possible accident outside the reclining furniture.

The warning devices described in the above publications emit a warning signal as soon as a person has left the reclining furniture completely or at least partially. However, even in the case of partially leaving the reclining furniture, for example when a user sits up, there is already a considerable risk of injury to some users of the reclining furniture. In addition, it takes time for the nursing staff to reach the location of the reclining furniture.

It is therefore an object of the present invention to create reclining furniture having at least one sensor and a warning device coupled to said sensor and a method for operating such a warning device, in which a danger to a user of the reclining furniture by leaving the reclining furniture can be excluded as securely as possible.

SUMMARY OF THE INVENTION

This object is solved by a reclining furniture or a method for operating a warning device of a reclining furniture having the features of the respective independent claim. Advantageous arrangements and further developments are the subject of the dependent claims.

A reclining furniture in accordance with the invention is characterized in that the warning device is designed to evaluate information from at least one sensor, which is arranged on the reclining furniture, with regard to a movement and/or behavior pattern of a person using the reclining furniture, in order to output a warning or information signal as soon as there is an intention to leave the reclining furniture.

Accordingly, a method for operating a warning device of a reclining furniture in accordance with the invention has the following steps:

Signals or data of at least one sensor, which is arranged at the reclining furniture or also in an environment of the reclining furniture, are detected and evaluated. On the basis of the evaluated sensor information, a movement and/or behavior pattern of a person using the reclining furniture is created. The pattern of movement and/or behavior is analyzed in order to identify an intention to leave the reclining furniture. If such an intention is detected, a warning or information signal is issued.

In contrast to the prior art, it is not the result of a partial or complete standing up that is recorded, but indications that indicate an impending standing up. Accordingly, a warning or information signal cannot only be issued when the person using the reclining furniture has already got up completely or partially but in advance. This gives the nursing staff more time to reach the location of the reclining furniture and to prevent or accompany the attempt to get up, thus protecting the person from possible accidents.

As a rule, especially in the case of elderly people or people in need of care, standing up from a reclining furniture from a relaxed sitting or lying position is associated with longer preparations in order to bring the body into a suitable position from which the actual standing up can be carried out. These preparations are announced in a movement and/or behavior pattern of the person that can be detected by the sensors. For example, before getting up, there is a movement cycle in which the body is moved with the application of force by means of the arms in the direction of a headboard (in the case of a bed) or in the direction of an inclined backrest (in the case of seating furniture).

Such a motion sequence can be detected, for example, by sensors arranged in the middle of a bed or in the armrests of an armchair. Movement and/or behavior patterns created from signals from the sensors can then be compared with predefined comparative patterns for analysis. Such comparative patterns can correspond to frequently observable movement sequences before getting up, with which the actual process of getting up is Initiated. In addition, patient-specific comparative patterns can be maintained to which the warning device can be trained. For this purpose, for example, at least one previously recorded and created actual movement and/or behavior pattern of a getting-up situation can be stored as a comparative pattern.

For this purpose, the reclining furniture or the warning device has at least one storage device in which the said comparative sample can be stored in the form of at least one data record and thus deposited. A first data set is formed as a factory data set and corresponds to a tried and tested comparative pattern, which also corresponds as an average comparative pattern to the movement or behavior pattern of different persons. The storage device can preferably record several comparative patterns. In addition, several storage devices may be provided as an alternative. Further alternatively, at least one storage device can be wired or wirelessly connected to the furniture or to the warning device. It is also possible to use a sequence of wired and wirelessly coupled storage devices in series, for example if a storage device spatially separated from the furniture is used in the form of a cloud. Another storage device that is physically separate from the furniture can be part of a furniture device, e.g. a smartphone or the like.

A warning signal is output in accordance with a preferred embodiment if the at feast one movement and/or behavior pattern matches the comparative pattern to a high degree. However, since ail detected and analyzed movement and/or behavior patterns naturally differ slightly from one another, a degree of agreement can be taken into account, wherein the warning signal is triggered when the degree of agreement is reached or exceeded. The degree of agreement indicates with which similarity the comparative pattern corresponds to the detected and analyzed motion and/or comparative pattern.

Furthermore, the degree of agreement can be changed within specified limits. It is also possible to change the degree of influence of individual sensors to determine and analyze the motion and/or behavior pattern within given limits. This degree and also alternatively the degree of agreement and similarly alternatively the duration of the predominant motion and/or behavior pattern or alternatively a time delay for the delayed output of the warning signal can be set by means of software. The setting is carried out in an exemplary embodiment by a smartphone, tablet computer, laptop or the like, wherein a software or app executable on it for the configuration and setting of such aforementioned parameters and degrees is designed to be communicatively connectable with the warning device.

For example, force sensors are suitable sensors for recording a movement and/or behavior pattern. A force sensor is principally designed to detect a weight force or a muscle force or the like. Although alternative types of force sensors are also subjected to weight or muscle forces, they output a quantitative signal as an electrical output that corresponds to the motion and behavior pattern. Preferably, several sensors are used, which are arranged at different positions in the reclining furniture. In particular, a chronological sequence of signals detected by one or more sensors may be relevant. The force sensors can be designed as pure pressure sensors or as acceleration or vibration sensors. In addition, a sensor can also be designed as a microphone to detect and evaluate airborne noise, since an attempt to get up is often accompanied by noises that indicate an effort.

The warning device can additionally be coupled to at least one further sensor, which is arranged externally from the reclining furniture. Such an external sensor can be, for example, a sound transducer, e.g. a microphone.

The following sensors can also be provided as alternatives: position sensors, heat sensors, motion detectors based on PR (Pyroelectric Infrared Sensor) or PIS (Passive Infrared Sensor), sensors for recording body-borne noise. Sensors in the form of piezo sensors, resistance sensors and capacitive sensors can also be used. All of these sensors can be used individually or in combination with each other.

The warning device can directly emit acoustic or optical warning signals. Alternatively or additionally, it is conceivable that warning signals are emitted in the form of data signals, for example via a Bluetooth or WLAN (wireless local area network) connection. Such warning signals are then available in the network and can also be passed on to the nursing staff in neighboring rooms, for example via a smartphone or a notification beeper.

A variety of the above-mentioned sensors are particularly preferably arranged in different elements of the reclining furniture. For example, sensors can be arranged in a backrest as well as in the area of a seat of a piece of seating furniture, as well as in the armrests. Seating furniture often also has a footrest, which must be folded down before getting up, which can also be detected by appropriate sensors.

Reclining furniture of the type mentioned is often equipped with an electromotive furniture drive for adjusting the reclining furniture. If this is the case, adjusted positions of various elements of the reclining furniture, such as the backrest or a footrest or an inclination adjustment of a seat, can also be detected. Certain settings, e.g. current positions taken by movable furniture parts, can be interpreted as an additional indication of an imminent standing-up manoeuver. Depending on the position of the electromotive furniture drive, different comparative patterns are preferred for the analysis of the recorded movement and behavior patterns.

In an alternative configuration, the warning device is designed as a switching device such that the warning signal is output in the form of a switching signal. For example, the warning device can be coupled to an electromotive furniture drive. Such an electromotive furniture drive serves to move at least one furniture component relative to another furniture component. The movement and/or behavior pattern or the comparison of this with a comparative pattern as described in more detail at the beginning, then causes an adjustment of a furniture component relative to another furniture component.

After the warning or switching signal has been triggered, it can be provided to support an attempt to stand up or make it more difficult by adjusting the furniture component. For example, by lifting the seat surface, a person resting in the furniture can be lifted to make getting up easier. This can happen, for example, if the movement and behavior pattern of a person in the furniture is recognized as intentional standing up.

If several actions are planned, e.g. the output of different warning signals or the switching of different adjustment processes, a selection option for these different actions can be provided. Such a selection can be made, for example, via an appropriate operating software or one or more switches. A program ("app") on a smartphone or tablet computer can serve as operating software.

In an alternative embodiment, the warning device is designed as a retrofit device which can be retrofitted to an existing piece of furniture.

In another alternative embodiment, the warning device is not arranged directly on the reclining furniture, but indirectly via a user of the reclining furniture. For example, the person at rest then preferably wears the warning device including at least one sensor close to the body, e.g. in the form of a device on the wrist or belt or on or in a piece of clothing. Alternatively, such a device may be suspended from the resting person. The structure and mode of operation of such a device, in particular with regard to the detection of the sensor signals, the creation and analysis of the movement and behavior pattern and the output of the warning signal, correspond to the previously described arrangement of the warning device and the at least one sensor on the reclining furniture, wherein the previously described embodiments are at least partially realized by this device designed as a mobile device. If the mobile device is equipped with an integrated sensor system, for example an accelerometer or a microphone, the description and use of these sensors corresponds to the description and use mentioned above and should not be repeated here. The warning device is now integrated in the mobile device, alternatively the mobile device forms the warning device. If the warning device is integrated in the mobile device, an executable program ("app") of the mobile device can be understood as a warning device. For simplicity's sake, such a mobile device can be designed as a smartphone.

BRIEF DESCRIPTION OF THE DRAWING

The invention is explained in more detail below by reference to an embodiment example shown in the drawing. The only FIGURE shows an exemplary reclining furniture with an electromotive furniture drive and a plurality of sensors.

DETAILED DESCRIPTION OF PREFERRED EMBODIMENTS

The FIGURE shows by way of example a (relaxing) armchair 1, i.e. a piece of seating furniture, as an example of a piece of reclining furniture. Armchair comprises a seat surface 2, a backrest 3 and armrests 4. Optionally, an extendable footrest may be provided, but in the example shown it is either absent or retracted.

Armchair 1 also has one or more electromotive furniture drives 5, one of which is dashed. For example, an inclination of the backrest 3 can be adjusted via the electromotive furniture drive 5 shown.

The armchair 1 has a warning device not shown here, which is coupled to a plurality of sensors 6, which are arranged behind an upholstery. In particular, if an electromotive furniture drive 5 is present, as in the present case, the warning device can be integrated into a control device of the electromotive furniture drive. For example, a power supply and/or a data connection, which the control unit of the electromotive furniture drive has anyway, can then be shared by the warning device.

In the example shown, six sensors 6 are arranged in the reclining furniture, two in the area of the seat surface 2, two in the backrest 3 and one in each armrest 4. The sensors 6 can be pressure or force sensors or acceleration sensors, which can also be used to detect a force or a force shock or a movement acting on the corresponding area.

The sensors 6 are detected and evaluated by the warning device. For example, a time-varying activation pattern of sensors 6 can be extracted from the sensor data and compared with general or person-specific patterns in a pattern comparison. If the comparison indicates the execution of a movement and/or behavior pattern associated with or initiating, a standing up process, the warning device may issue a corresponding warning signal directly or via the aforementioned data links.

Depending on the position of the electromotive furniture drive(s) 5, different comparative patterns and/or comparison thresholds may be used as a basis, since different movement and behavior patterns are to be expected during a standing up process or the initiation of a standing up process, depending on the initial arrangement of the various components of the reclining furniture (e.g. inclination of the seat surface 2 and the backrest 3).

The pattern comparison can be based on the principles of a fuzzy logic in order to take into account a natural fluctuation, which will also show a repeated motion sequence. An evaluation in the form of a neural network—possibly implemented by a computer—is also possible.

What is claimed is:

1. A reclining furniture, comprising:
an electromotive furniture drive having positions to adjust elements of the reclining furniture;
a storage device in which predetermined comparative patterns are stored;
a plurality of sensors arranged on the reclining furniture providing information regarding a person using the reclining furniture and the positions of the electromotive furniture device; and
a warning device operably connected to the plurality of, sensors and the electromotive furniture drive for warning of an undesirable rising by the person using the reclining furniture, said warning device being configured to evaluate the information of the plurality of sensors with respect to a movement and/or behavior pattern of the person using the reclining furniture and the positions of the electromotive furniture drive and comparing the movement and/or behavior pattern with different predetermined comparative patterns depending on the positions of the electromotive furniture drive for analysis in order to emit a warning signal at a time when the person using the reclining furniture intends to leave the reclining furniture.

2. The reclining furniture of claim 1, wherein the sensors are a force sensor, a pressure sensor, an acceleration sensor and/or a vibration sensor.

3. The reclining furniture of claim 1, wherein the plurality of sensors is distributed upon various components of the reclining furniture.

4. The reclining furniture of claim 1, wherein the reclining furniture is constructed as a seating furniture.

5. The reclining furniture of claim 1, wherein the reclining furniture is constructed as armchair.

6. The reclining furniture of claim 1, wherein the plurality of sensors is arranged in a region of a seat surface, a backrest, an arm support and/or a foot part.

7. The reclining furniture of claim 1, wherein the warning device is configured to emit an audible and/or visual warning signal as the warning signal.

8. The reclining furniture of claim 1, wherein the warning device is configured to emit a data signal as the warning signal.

9. The reclining furniture of claim 1, further comprising a further sensor arranged externally from the reclining furniture, said warning device being operably connected to the further sensor.

10. The reclining furniture of claim 9, wherein the further sensor is a sound sensor.

11. A method, for operating a warning device of a reclining furniture, said method comprising:
acquiring a signal from a sensor arranged on the reclining furniture;
evaluating the acquired signal;
creating a movement and/or behavior pattern of a person using the reclining, furniture based on the evaluated signal;
analyzing the pattern of movement and/or behavior to determine whether there is any intention by the person to leave the reclining furniture;
emitting a warning signal when detecting the intention by the person to leave the reclining furniture;
wherein the movement and/or behavior pattern is created based on a temporal sequence of signals which have been detected by various sensors; and
wherein different comparative patterns are used for analysis of the movement and/or behavior pattern, depending on positions of an electromotive furniture drive provided for adjustment of elements of the reclining furniture.

12. The method of claim 11, further comprising comparing the created movement and/or behavior pattern with predetermined comparative patterns for analysis.

13. The method of claim 12, wherein at least one of the predetermined comparative patterns is generated from one of a plurality of created patterns of movement and/or behavior.

14. A method for operating a warning device of a reclining furniture, said method comprising:
   acquiring a signal from a senor arranged on the reclining furniture:
   evaluating the acquired signal;
   creating a movement and/or behavior pattern of a person using the reclining furniture based on the evaluated signal;
   analyzing the pattern of movement and/or behavior to determine whether there is any intention by the person to leave the reclining furniture;
   emitting a warning signal when detecting the intention by the person to leave the reclining furniture;
   further comprising comparing the created movement and/or behavior pattern with predetermined comparative patterns for analysis; and
   wherein different comparative patterns are used for analysis, depending on positions of an electromotive furniture drive provided for adjustment of elements of the reclining furniture.

15. The method of claim 14, wherein at least one of the predetermined comparative patterns is generated from one of a plurality of created patterns of movement and/or behavior.

\* \* \* \* \*